United States Patent [19]

Gebauer et al.

[11] Patent Number: 4,842,853
[45] Date of Patent: Jun. 27, 1989

[54] SOLID WHICH RELEASES A FRAGRANT SUBSTANCE AND/OR A DISINFECTANT

[75] Inventors: Helmut Gebauer, Munich; Franz-Heinrich Kreuzer, Martinsried, both of Fed. Rep. of Germany

[73] Assignee: Consortium für Elektrochemische, Munich, Fed. Rep. of Germany

[21] Appl. No.: 892,547

[22] Filed: Aug. 4, 1986

Related U.S. Application Data

[60] Division of Ser. No. 721,141, Apr. 9, 1985, abandoned, Continuation of Ser. No. 524,007, Aug. 17, 1983, abandoned.

[30] Foreign Application Priority Data

May 27, 1983 [EP] European Pat. Off. ........ 83105270.9

[51] Int. Cl.$^4$ .......................... A61L 9/01; A61L 13/00
[52] U.S. Cl. .................................................... 424/76.1
[58] Field of Search ........................................... 424/76

[56] References Cited

U.S. PATENT DOCUMENTS

| | | | |
|---|---|---|---|
| 1,408,535 | 3/1922 | Ressler | 424/76 |
| 4,009,684 | 7/1977 | Kliment et al. | 424/76 |
| 4,045,551 | 8/1977 | Ueno et al. | 424/76 |
| 4,250,165 | 2/1981 | Foley | 424/76 |

OTHER PUBLICATIONS

Translation of Kumagai et al., Kokai, 54–46847, (79–46847), Apr. 1979.

*Primary Examiner*—Leonard Schenkman

[57] ABSTRACT

A solid which contains a fragrant substance and/or a disinfectant and at least one sublimable substance, in which the sublimable substance consists at least in part of hexamethylcyclotrisiloxane and/or tetramethylcyclobutanedione. When the solid is exposed to the environment, it releases the fragrant substance and/or disinfectant.

9 Claims, No Drawings

SOLID WHICH RELEASES A FRAGRANT SUBSTANCE AND/OR A DISINFECTANT

This ia a, division, of application, Ser. No. 721,141 filed Apr. 9, 1985, which is a continuation of application Ser. No. 524,007, filed August 17, 1983 both abd.

The present invention relates to a solid which releases a fragment substance and/or a disinfectant and more particularly to a solid which contains, in addition to the fragrant substance and/or a disinfectant, a sublimable carrier which when exposed to the environment releases the fragrant substance and/or disinfectant.

BACKGROUND OF THE INVENTION

Heretofore, para-dichlorobenzene has been used to form deodorizer blocks for use in restrooms. (See Seifen-Oele-Fette-Wachse, Vol. 108 p.529). Since para-dichlorobenzene is moderately toxic, it is desirable to find a substitute for this material.

Therefore, it is an object of the present invention to provide a solid which will release a fragrant substance when exposed to the environment. Another object of the present invention is to provide a solid which will release a disinfectant to the environment. Still another object of the present invention is to provide a solid containing a fragrant substance and/or a disinfectant and a sublimable carrier for the fragrant substance and/or disinfectant. A further object of this invention is to find a substitute for para-dichlorobenzene as a deodorizer which is less toxic.

SUMMARY OF THE INVENTION

The foregoing objects and others which will become apparent from the following description are accomplished in accordance with this invention, generally speaking, by providing a solid containing a fragrant substance and/or a disinfectant and a sublimable carrier in which at least a portion of the sublimable carrier is selected from the group consisting of hexamethylcyclotrisiloxane, tetramethylcyclobutanedione and mixtures thereof, which when exposed to the environment releases the fragrant substance and/or disinfectant.

DESCRIPTION OF THE INVENTION

The solid prepared in accordance wtih this invention is suitable not only as a fragrance block for use in restrooms, but it is indeed suitable for the release of fragrant substances or disinfectants or fragrant substances and disinfectants, for example, in waiting rooms of any type, such as livng rooms, workroom, and lounges, as well as rooms in which objects are displayed or performances held, and public and private washrooms.

The solid of this invention can be support-free or it can be supported by supports such as paper, cardboard, or plastic films or it can contain such supports or be supported in containers which have at least one opening.

The solid can contain the same fragrant substances and disinfectants or the same fragrant substances or disinfectants as the previously known solids for the release of fragrant substances and/or disinfectants to the surrounding environment such as air or water.

One of the sublimable carriers contemplated by this invention for the fragrant substances and/or disinfectants is hexamethylcyclotrisiloxane. Hexamethylcyclotrisiloxane, which is a known compound, has been combined with fragrant substances and used heretofore in cosmetics. (See, for example, Chemical Abstracts, Vol. 91, 1979, Abstract 198797 k).

Hexamethylcyclotrisiloxane can be prepared in accordance with known methods or it can be prepared by heating a linear, branched, or cross-linked organopolysiloxane which consists of at least 50 mol percent of dimethylsiloxane units to at least 350° C. in the absence of substantial amounts of substances which attack the siloxane group, and simultaneously distilling off the cyclic dimethylpolysiloxanes formed during heating.

The sublimation rate of hexamethylcyclotrisiloxane, which is higher than that of p-dichlorobenzene, can be controlled by adjusting the size of the openings of the container in which the hexamethylcyclotrisiloxane, together with the fragrant substance and/or disinfectant, is exposed to the environment or by admixing a slow-subliming substance such as tetramethylcyclobutanedione with the hexamethylcyclotrisiloxane. A mixture containing 25 weight percent of hexamethylcyclotrisiloxane and 75 weight percent of tetramethylcyclobutanedione has about the same rate of sublimation as p-dichlorobenzene.

Tetramethylcyclobutanedione which is a known compound has the formula

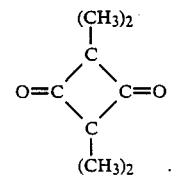

Tetramethylcyclobutanedione is preferred when the solid is to be exposed in the presence of water, such as for example, when the solid is to be used in toilet fixtures.

Tetramethylcyclobutanedione has a pleasant wood-camphor odor, and is capable of binding basic substances such as ammonia.

If the solid of this invention contains both hexamethylcyclotrisiloxane and tetramethylcyclobutanedione, it preferably contains from 10 to 90 weight percent and more preferably from 20 to 30 weight percent of hexamethylcyclotrisiloxane and from 90 to 10 weight percent and more preferably from 80 to 70 weight percent of tetramethylcyclobutanedione, based on the total weight of hexamethylcyclotrisiloxane and tetramethylcyclobutanedione.

Preferably, the solid of this invention contains from 5 to 20 weight percent of a fragrant substance or disinfectant, based on the weight of the hexamethylcyclotrisiloxane, when the sublimable substances other than the fragrant substance or disinfectant consists of at least 50 weight percent hexamethylcyclotrisiloxane. When the fragrant substance or disinfectant is a solid the fraction of sublimable can also be larger.

Preferably, the solid of this invention contains from 5 to 20 weight percent of a fragrant substance or disinfectant, based on the weight of the tetramethylcyclobutanedione, when the sublimable substance other than fragrant substance or disinfectant consists of at least 50 weight percent tetramethylcyclobutanedione.

The solid prepared in accordance with this invention can contain other substances in addition to the hexamethylcyclotrisiloxane and/or tetramethylcyclobutanedione and the fragrant substance and/or disinfectant. The addition of the other substances makes it possible to add even greater amounts of fragrant substances and/or disinfectants than that indicated above. Examples of such other substances are pyrogenic silica or precipitated silica having a surface area of at least 50 m$^2$/g, common salt, surfactants, insect repellents, deodorants, and dyes, as well as phosphates. The amount of silica having a surface area of at least 50 m$^2$/g is preferably from 0.5 to 5 weight percent, based on the total weight of the solid.

Hexamethylcyclotrisiloxane and tetramethylcyclobutanedione can be mixed as powders or melts with the other components to form the deodorizer compositions of this invention.

In the following examples, all parts and percentages are by weight unless otherwise specified.

EXAMPLE 1

About 20 g of pulverized hexamethylcyclotrisiloxane are blended with 2 g of perfume oil ("Sea Breeze", Dragoco) and molded into a cylinder. The cylinder thus formed is placed in a plastic container of corresponding size which has a large number of small openings. The contents of the plastic container are effective as a room air deodorizer until they are completely volatilized (25 days).

EXAMPLE 2

About 20 g of a hexamethylcyclotrisiloxane melt is blended with 2 g of orange terpenes and solidified in a round mold. The cylinder obtained in this manner is placed in a plastic container of corresponding size which has a large number of small openings. The contents of the plastic container remain effective as a room air deodorizer until they have completely volatilized (25 days).

EXAMPLE 3

About 18 g of pulverized hexamethylcyclotrisiloxane are blended at 60° C. with 12 g of "Lilac" perfume oil and 1 g of pyrogenic silica having a surface area of approximately 200 m$^2$/g, and the melt thus formed is solidified in a polystyrene petri dish containing longitudinal slots in its top. The contents of the petri dish give off a pleasant odor for 28 days in a room measuring 45 m$^3$.

| Composition of the "Lilac" perfume oil | |
|---|---|
| 18.0 percent | Hydroxycitronellal |
| 1.7 percent | Cinnamyl alcohol |
| 8.0 percent | Terpineol |
| 18.0 percent | Benzyl alcohol |
| 20.0 percent | Phenethyl alcohol |
| 2.0 percent | Linalool |
| 0.5 percent | Phenylacetaldehyde |
| 6.0 percent | Anisaldehyde |
| 16.0 percent | Piperonal |
| 2.5 percent | Indole (10 percent) |
| 7.3 percent | Jasmine base |

EXAMPLE 4

A mixture containing 10 g of pulverized hexamethylcyclotrisiloxane, 30 g of tetramethylcyclobutanedione and 5 g of a lily of the valley composition is molded into a cube. The cube is hung loose in a room and remains effective as a room deodorizer until it has completely volatilized (23 days).

| Lily of the valley composition | |
|---|---|
| | Parts |
| Hydroxycitronellal | 50 |
| a-Hexylcinnamaldehyde | 4 |
| Benzyl alcohol | 4 |
| Geraniol | 3 |
| Citronellol | 3 |
| Linalool | 3 |
| Citronellal | 3 |
| Linalyl acetate | 2 |
| Indole (10 percent) | 1 |
| cis-3-Hexenol (10 percent) | 1 |
| Lauryl aldehyde (10 percent) | 1 |

EXAMPLE 5

About 45 g of pulverized tetramethylcyclobutanedione is blended with 7 g of lavender oil and molded into a cylinder. The cylinder thus obtained gives off a pleasant fresh odor until it has completely volatilized (68 days).

EXAMPLE 6

A mixture containing

| 60 percent | Tetramethylcyclobutanedione |
|---|---|
| 20 percent | Sodium chloride |
| 15 percent | Fragrant substance |
| 1 percent | Bactericide ("Preventol", registered trademark, Bayer AG) |
| 4 percent | Pyrogenic silica having a surface area of approximately 200 m$^2$/g | is molded into a block weighing 10 g. The fragrance block thus obtained is used in toilet bowls. It eliminates odors for 29 days just as thoroughly as a 50 g fragrance block containing p-dichlorobenzene.

EXAMPLE 7

Molded fragrance blocks weighing 70 g which consists of

| 50 parts | tetramethylbutanedione |
|---|---|
| 20 parts | phosphates |
| 20 parts | surfactants and a total of |
| 10 parts | bactericide, aromatic substance and dye | clean, disinfect, give off a fragrance, and eliminate undesirable odors in toilet bowls for 3 to 6 weeks, depending on the frequency of flushing.

What is claimed is:

1. A solid which releases a fragrant substance and/or a disinfectant to the environment comprising a substance selected from the group consisting of a fragrant substance, a disinfectant and mixtures thereof and a sublimable carrier in which at least a portion of the sublimable carrier is a mixture consisting of from 10 to 90 weight percent of hexamethylcyclotrisiloxane and from 90 to 10 weight percent of tetramethylcyclobutanedione based on the weight of hexamethylcyclotrisiloxane and tetramethylcyclobutanedione.

2. The solid of claim 1, wherein the sublimable carrier contains from 20 to 30 weight percent of hexamethylcyclotrisiloxane and from 80 to 70 weight percent of tetramethylcyclobutandione, based on the weight of the hexamethylcyclotrisiloxane and tetramethylcyclobutanedione.

3. The solid of claim 1, wherein the sublimable carrier contains at least 50 weight percent of hexamethylcyclotrisiloxane and the fragrant substance is perfume oil, in which the perfume oil is present in an amount of from 5 to 20 weight percent based on the weight of the hexamethylcyclotrisiloxane.

4. The solid of claim 1, wherein the sublimable carrier contains at least 50 weight percent of tetramethylcyclobutanedione and the fragrant substance is perfume oil, in which the perfume oil is present in an amount of from 5 to 20 weight percent based on the weight of the tetramethylcyclobutanedione.

5. A method for releasigng a substance to the environment which comprises exposing a solid composition containing a sublimable carrier in which at least a portion of the sublimable carrier consists of from 10 to 90 weight percent of hexamethylcyclotrisiloxane and from 90 to 10 weight percent of tetramethylcyclobutanedione based on the weight of the hexamethylcyclotrisiloxane and tetramethylcyclobutanedione and a substance selected from the group consisting of a fragrant substance, a disinfectant and mixtures thereof to the environment.

6. The method of claim 5, wherein the sublimable carrier contains at least 50 weight percent of hexamethylcyclotrisiloxane and the fragrant substance is perfume oil, in which the perfume oil is present in an amount of from 5 to 20 weight percent based on the weight of the hexamethylcyclotrisiloxane.

7. The method of claim 5, wherein the sublimable carrier contains at least 50 weight percent of tetramethylcyclobutanedione and the fragrant substance is perfume oil, in which the perfume oil is present in an amount of from 5 to 20 weight percent based on the weight of the tetramethylcyclobutanedione.

8. The method of claim 5, wherein the solid composition is exposed to water.

9. The method of claim 5, wherein the solid composition is exposed to air.

* * * * *